(12) United States Patent
Weinshilboum et al.

(10) Patent No.: US 7,674,583 B2
(45) Date of Patent: Mar. 9, 2010

(54) ALTERATIONS IN THE COPY NUMBER OF THE SULT1A1 GENE

(75) Inventors: Richard M. Weinshilboum, Rochester, MN (US); Araba A. Adjei, Rochester, MN (US); Scott J. Hebbring, Rochester, MN (US); Stephen N. Thibodeau, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 28 days.

(21) Appl. No.: 11/559,548

(22) Filed: Nov. 14, 2006

(65) Prior Publication Data

US 2007/0178493 A1    Aug. 2, 2007

Related U.S. Application Data

(63) Continuation-in-part of application No. 11/297,712, filed on Dec. 8, 2005.

(51) Int. Cl.
*C12Q 1/68* (2006.01)
*C12P 19/34* (2006.01)
*C07H 21/02* (2006.01)

(52) U.S. Cl. .................... 435/6; 435/91.2; 536/23.1

(58) Field of Classification Search .................. None
See application file for complete search history.

(56) References Cited

U.S. PATENT DOCUMENTS

2007/0134675 A1*  6/2007  Hebbring et al. ............... 435/6

OTHER PUBLICATIONS

Jüppner H., 'Functional properties of the PTH/PTHrP receptor'. Bone. Aug. 1995;17(2 Suppl):39S-42S.*
Honma W et al 'Enzymatic characterization and interspecies difference of phenol sulfotransferases, ST1A forms.' Drug Metab Dispos. Mar. 2001;29(3):274-81.*
Orntoft TF et al 'Genome-wide Study of Gene Copy Numbers, Transcripts, and Protein Levels in Pairs of Non-invasive and Invasive Human Transitional Cell Carcinomas' Mol Cell Proteomics. Jan. 2002;1(1):37-45.*
Chan E 'Integrating Transcriptomics and Proteomics' G & P magazine: vol. 6, No. 3, Apr. 2006, pp. 20-26. printed pp. 1-6 provided.*
Bamber DE et al Pharmacogenetics 2001, vol. 11 No. 8, pp. 679-685.*
Spink BC et al Carcinogenesis 2000, vol. 21 No. 11 pp. 1947-1957.*
Gjerde J et al 'Effects of CYP2D6 and SULT1A1 genotypes including SULT1A1 gene copy number on tamoxifen metabolism.' Ann Oncol. Jan. 2008;19(1):56-61.*
Hildebrandt MA et al 'Human SULT1A3 pharmacogenetics: gene duplication and functional genomic studies.' Biochem Biophys Res Commun. Sep. 3, 2004;321(4):870-8.*
GenBank Locus HSU52852 'Homo sapiens TS PST1 (STP1) gene, complete cds', Mar. 13, 2001, from www.ncbi.nlm.nih.gov, pp. 1-5.*
Raftogiansis R et al 'Human phenol sulfotransferases SULT1A2 and SULT1A1: genetic polymorphisms, allozyme properties, and human liver genotype-phenotype correlations.' Biochem Pharmacol. Aug. 15,1999;58(4):605-16.*
Duanmu Z et al 'Transcriptional regulation of rat hepatic aryl sulfotransferase (SULT1A1) gene expression by glucocorticoids.' Drug Metab Dispos. Aug. 2001;29(8):1130-5.*
Chiang PW et al 'Use of a fluorescent-PCR reaction to detect genomic sequence copy number and transcriptional abundance.' Genome Res. 1996 6: 1013-1026.*
Wolf S et al 'Direct visual resolution of gene copy number in the human photopigment gene array.' Invest Ophthalmol Vis Sci. Jun. 1999;40(7):1585-9.*
Schouten JP et al 'Relative quantification of 40 nucleic acid sequences by multiplex ligation-dependent probe amplification.' Nucleic Acids Res. Jun. 15, 2002;30(12):e57. pp. 1-13.*
Wang Y et al 'A modified multiplex PCR assay for detection of large deletions in MSH2 and MLH1.' Hum Mutat. Mar. 2002;19(3):279-86.*
Johansson I. et al. Proc. Natl. Acad. Sci. USA (1993) vol. 90, pp. 11825-11829.*
GenBank Accession No. AB062428 dated May 23, 2002, 2 pages.
GenBank Accession No. NM_003166 dated Sep. 3, 2007, 5 pages.
GenBank Accession No. NM_177528 dated Sep. 25, 2007, 5 pages.
GenBank Accession No. U20499 dated Mar. 29, 1995, 5 pages.
GenBank Accession No. U28170 dated Oct. 2, 1996, 2 pages.
GenBank Accession No. U52852 dated Mar. 13, 2001, 5 pages.
Adjei and Weinshilboum, "Catecholestrogen Sulfation: Possible Role in Carcinogenesis," *Biochem. Biophys. Res. Commun.*, 2002, 292:402-408.
Agúndez et al., "Prevalence of *CYP2D6* gene duplication and its repercussion on the oxidative phenotype in a white population," *Clin. Pharmacol. Ther.*, 1995, 57(3):265-269.
Aklillu et al., "Frequent Distribution of Ultrarapid Metabolizers of Debrisoquine in an Ethiopian Population Carrying Duplicated and Multiduplicated Functional *CYP2D6* Alleles," *J. Pharmacol. Exp. Ther.*, 1996, 278(1):441-446.
Anderson et al., "Human platelet thermostable phenol sulfotransferase from blacks and whites: Biochemical properties and variations in thermal stability," *J. Lab. Clin. Med.*, 1988, 112:773-783.
Bertilsson et al., "Molecular basis for rational megaprescribing in ultrarapid hydroxylators of debrisoquine," *Lancet*, 1993, 341:63, Abstract.
Bunyan et al., "Dosage analysis of cancer predisposition genes by multiplex ligation-dependent probe amplification," *Br. J. Cancer*, 2004, 91:1155-1159.
Campbell et al., "Human liver phenol sulfotransferase: assay conditions, biochemical properties and partial purification of isozymes of the thermostable form," *Biochem. Pharmacol.*, 1987, 36(9):1435-1446.

(Continued)

Primary Examiner—Stephen Kapushoc
(74) Attorney, Agent, or Firm—Fish & Richardson P.C.

(57) ABSTRACT

Methods are described for determining sulfonator status of a patient and determining dosages of drugs based on copy number of the SULT1A1 gene.

8 Claims, 5 Drawing Sheets

OTHER PUBLICATIONS

Carlini et al., "Sulfation pharmacogenetics: *SULT1A1* and *SULT1A2* allele frequencies in Caucasian, Chinese and African-American subjects," *Pharmacogenetics*, 2001, 11:57-68.

Casilli et al., "Rapid Detection of Novel *BRCA1* Rearrangements in High-Risk Breast-Ovarian Cancer Families Using Multiplex PCR of Short Fluorescent Fragments," *Hum. Mutat.*, 2002, 20:218-226.

Coughtrie, "Sulfation through the looking glass—recent advances in sulfotransferase research for the curious," *Pharmacogenomics J.*, 2002, 2:297-308.

Dalén et al., "10-Hydroxylation of nortriptyline in white persons with 0, 1, 2, 3, and 13 functional *CYP2D6* genes," *Clin. Pharmacol. Ther.*, 1998, 63(4):444-452.

Foldes and Meek, "Rat brain phenolsulfotransferase—partial purification and some properties," *Biochim. Biophys. Acta*, 1973, 327:365-374.

Gaedigk et al., "Deletion of the Entire Cytochrome P450 CYP2D6 Gene as a Cause of Impaired Drug Metabolism in Poor Metabolizers of the Debrisoquine/Sparteine Polymorphism," *Am. J. Hum. Genet.*, 1991, 48(5):943-950.

Glatt and Meinl, "Pharmacogenetics of soluble sulfotransferases (SULTs)," *Naunyn-Schmiedeberg's Arch. Pharmacol.*, 2004, 369:55-68.

Glatt, "Sulfotransferases in the bioactivation of xenobiotics," *Chemico-Biol. Interact.*, 2000, 129:141-170.

Gough et al., "Identification of the primary gene defect at the cytochrome $P_{450}$ *CYP2D* locus," *Nature*, 1990, 347:773-776.

Han et al., "Sulfotransferase 1A1 (*SULT1A1*) polymorphism and breast cancer risk in Chinese women," *Toxicol. Lett.*, 2004, 150:167-177.

Hebbring et al., "Human *SULT1A1* gene: copy number differences and functional implications," *Human Mol. Genet.*, 2007, 16(5):463-470.

Her et al., "Human Phenol Sulfotransferase *STP2* Gene: Molecular Cloning, Structural Characterization, and Chromosomal Localization," *Genomics*, 1996, 33:409-420.

Herrick et al., "Quantifying single gene copy number by measuring fluorescent probe lengths on combed genomic DNA," *Proc. Natl. Acad. Sci. USA*, 2000, 97(1):222-227.

Hildebrandt et al., "Human *SULT1A3* pharmacogenetics: gene duplication and functional genomic studies," *Biochem. Biophys. Res. Commun.*, 2004, 321(4):870-878.

Hollox et al., "DNA copy number analysis by MAPH: molecular diagnostic applications," *Expert. Rev. Mol. Diagn.*, 2002, 2(4):370-378.

Johansson et al., "Inherited amplification of an active gene in the cytochrome P450 *CYP2D* locus as a cause of ultrarapid metabolism of debrisoquine," *Proc. Natl. Acad. Sci. USA*, 1993, 90:11825-11829.

Langsenlehner et al., "Genetic variants of the sulfotransferase 1A1 and breast cancer risk," *Breast Cancer Res. Treat.*, 2004, 87:19-22.

Lee et al., "Rapid detection of trisomy 21 by homologous gene quantitative PCR (HGQ-PCR)," *Hum. Genet.*, 1997, 99:364-367.

Ning et al., "Common genetic polymorphisms in the 5'-flanking Region of the *SULT1A1* gene: haplotypes and their association with platelet enzymatic activity," *Pharmacogenet. Genomics*, 2005, 15:465-473.

Nowell et al., "Relationship of phenol sulfotransferase activity (*SULT1A1*) genotype to sulfotransferase phenotype in platelet cytosol," *Pharmacogenetics*, 2000, 10:789-797.

Nowell et al., "Association of SULT1A1 Phenotype and Genotype with Prostate Cancer Risk in African-Americans and Caucasians," *Cancer Epidemiol. Biomarkers Prev.*, 2004, 13:270-276.

Ozawa et al., "Sulfating-Activity and Stability of cDNA-Expressed Allozymes of Human Phenol Sulfotransferase, ST1A3*1 ($^{213}$Arg) and ST1A3*2 ($^{213}$His), Both of Which Exist in Japanese as Well as Caucasians," *J. Biochem.*, 1999, 126:271-277.

Pertl et al., "Rapid detection of chromosome aneuploidies by quantitative fluorescence PCR: first application on 247 chorionic villus samples," *J. Med. Genet.*, 1999, 36:300-303.

Price et al., "Genetic Polymorphism for Human Platelet Thermostable Phenol Sulfotransferase (TS PST) Activity," *Genetics*, 1989, 122:905-914.

Prondzinski et al., "Sulfotransferase (SULT) 1A1 pharmacogenetics: Functional 5'-flanking region (5'-FR) polymorphisms," *Clinical Pharmacology and Therapeutics*, 2003, 73(2):77, Abstract.

Raftogianis et al., "Human Phenol Sulfotransferases *SULT1A2* and *SULT1A1*: Genetic polymorphisms, allozyme properties, and human liver genotype-phenotype correlations," *Biochem. Pharmacol.*, 1999, 58:605-616.

Raftogianis et al., "Human phenol sulfotransferase pharmacogenetics: *STP1** gene cloning and structural characterization," *Pharmacogenetics*, 1996, 6:473-487.

Raftogianis et al., "Phenol sulfotransferase pharmacogenetics in humans: association of common SULT1A1 alleles with TS PST phenotype," *Biochem. Biophys. Res. Commun.*, 1997, 239(1):298-304.

Ruiz-Ponte et al., "Rapid Real-Time Fluorescent PCR Gene Dosage Test for the Diagnosis of DNA Duplications and Deletions," *Clin. Chem.*, 2000, 46:1574-1582.

Saintot et al., "Interactions between genetic polymorphism of cytochrome P450-1B1, sulfotransferase 1A1, catechol-*O*-methyltransferase and tobacco exposure in breast cancer risk," *Int. J. Cancer*, 2003, 107:652-657.

Schouten et al., "Relative quantification of 40 nucleic acid sequences by multiplex ligation-dependent probe amplification," *Nucleic Acids Res.*, 2002, 30(12):e57, 13 pages.

Sprenger et al., "Characterization of the glutathione *S*-transferase *GSTT1* deletion: discrimination of all genotypes by polymerase chain reaction indicates a trimodular genotype-phenotype correlation," *Pharmacogenetics*, 2000, 10:557-565.

Van Loon and Weinshilboum, "Human Platelet Phenol Sulfotransferase: Familial Variation in Thermal Stability of the TS Form," *Biochem Genet.*, 1984, 22(11-12):997-1014.

Weinshilboum, "Inheritance and Drug Response," *N. Engl. J. Med.*, 2003, 348(6):529-537.

Xu et al., "Characterization of the Human Class Mu Glutathione *S*-Transferase Gene Cluster and the *GSTM1* Deletion," *J. Biol. Chem.*, 1998, 273(6):3517-3527.

Yan et al., "Genetic Diganosis: Conversion of diploidy to haploidy," *Nature*, 2000, 403:723-724.

Zheng et al., "Sulfotransferase 1A1 (*SULT1A1*) polymorphism and bladder cancer risk: a case-control study," *Cancer Lett.*, 2003, 202:61-69.

Kahlem et al., "Transcript level alterations reflect gene dosage effects across multiple tissues in a mouse model of Down Syndrome," *Genome Res.*, 14:1258-1267, 2004.

Yang et al., "Organismal complexity, protein complexity and gene duplicability," *Proc. Natl. Acad. Sci. U.S.A.*, 100(26):15661-15665, 2003.

* cited by examiner

ALTERATIONS IN THE COPY NUMBER OF THE SULT1A1 GENE

CROSS-REFERENCE TO RELATED APPLICATIONS

This application is a continuation-in-part of U.S. Ser. No. 11/297,712, filed Dec. 8, 2005.

STATEMENT AS TO FEDERALLY SPONSORED RESEARCH

This invention was made with government support under grant nos. GM35720 and CA91956-05P1 awarded by the National Institutes of Health. The government has certain rights in the invention.

TECHNICAL FIELD

This invention relates to methods and materials for determining copy number of a gene, and more particularly, to methods and materials for determining the copy number of the SULT1A1 gene, and assessing the sulfonator status of a subject based on SULT1A1 copy number.

BACKGROUND

Cytosolic sulfotransferase superfamilies (SULTs) act on a wide variety of natural and synthetic chemicals. With the wide tissue distribution, extensive substrate affinity, involvement in the detoxification and metabolism of numerous drug compounds, hormones and xenobiotics, and the participation in the bioactivation of environmental and dietary procarcinogens, the SULT1A1 gene has been the most widely studied. Glatt (2000) *Chem. Biol. Interact.* 129(1-2):141-170.

SULT1A1 is one of four SULT1A genes located on chromosome 16 that share at least 93% amino acid sequence identity. Her et al. (1996) *Genomics* 33(3): 409-20; Raftogianis et al. (1996) *Pharmacogenetics* 6(6): 473-87; and Hildebrandt et al. (2004) *Biochem. Biophys. Res. Commun.* 321(4): 870-8. Three non-synonymous single nucleotide polymorphisms (SNPs) divide the SULT1A1 gene into four alleles: SULT1A1*1 (wildtype), SULT1A1*2 (Arg213His), SULT1A1*3 (Met223Val), and SULT1A1*4 (Arg37Gln). The two most common alleles found among most populations are the 1A1*1 and 1A1*2 alleles. Subjects homozygous for 1A1*2 are thought to have an 85% reduction in platelet phenol sulfotransferase activity and a decrease in thermal stability compared to subjects that are heterozygous for 1A1*1/1A1*2 or homozygous for 1A1*1. See Raftogianis et al. (1997) *Biochem. Biophys. Res. Commun.*, 239(1):298-304; and Raftogianis et al. (1999) *Biochem. Pharmacol.,* 58(4): 605-16.

Langsenlehner et al. (2004, *Breast Cancer Res. Treat.,* 87(1):19-22) showed that in their breast cancer population, the 1A1*2 allele was associated with lymph node metastasis but not with breast cancer itself. Saintot et al. (2003, *Int. J. Cancer,* 107(4):652-7) also found no association of the 1A1*2 allele to breast cancer in the population they studied; however they observed that the 1A1*2 allele increased the risk for breast cancer if one smoked. Within a Chinese population, the frequency of the 1A1*2 allele in women with breast cancer was statistically significant compared to a control set. Han et al. (2004) *Toxicol. Lett.,* 150(2):167-77. Conversely, in other studies, the 1A1*1 allele may be associated with prostate and bladder cancer. Nowell et al. (2004) *Cancer Epidemiol. Biomarkers Prev.,* 13(2):270-6; and Zheng et al. (2003) *Cancer Lett.,* 202(1):61-9. Based on these variable results, other factors may play a critical role in SULT1A1's function and involvement with certain types of cancers.

SUMMARY

The invention is based on the discovery that the copy number of the SULT1A1 gene is altered in at least 30% of the human subjects studied. Deletions or duplications of the SULT1A1 gene can result in alteration in SULT1A1 activity, and consequently, the administration of improper dosages of drugs to patients or an increased risk of cancer as SULT1A1 is involved in the detoxification and metabolism of numerous drugs, hormones, and xenobiotics, and participates in the bioactivation of environmental and dietary procarcinogens.

In one aspect, the invention features a method of determining sulfonator status of a patient. The method includes providing a biological sample from the patient; determining copy number of the SULT1A1 gene in the biological sample (e.g., a blood or tissue sample); and correlating copy number of the SULT1A1 gene with sulfonator status of the patient. Copy number can be determined by analyzing DNA, RNA or protein. For example, copy number of the SULT1A1 gene can be detected by a quantitative PCR assay such as a fluorescent quantitative PCR assay, fluorescence in situ hybridization, Southern blotting, multiplex ligation-dependent probe amplification (MLPA), or Quantitative Multiplex PCR of Short Fluorescent Fragments (QMPSF). Copy number also can be detected by Northern blotting or Western blotting.

In another aspect, the invention features a method for determining the dosage of a drug to be administered to a patient, wherein the drug is a substrate of SULT1A1. The method includes providing a biological sample (e.g., blood or tissue sample) from the patient; determining copy number of the SULT1A1 gene in the biological sample; and determining the dosage of the drug based, at least in part, on the copy number of the SULT1A1 gene. An increase in the copy number of the SULT1A1 gene can result in an increased dosage of the drug, whereas a decrease in copy number of the SULT1A1 gene can result in a decreased dosage of the drug. Copy number of the SULT1A1 gene can be determined by a fluorescent quantitative PCR assay, fluorescence in situ hybridization, Southern blotting, MLPA, or QMPSF. The drug can be a monocyclic phenol, epinephrine, acetaminophen, or minoxidil.

The invention also features an article of manufacture that includes a first oligonucleotide primer and a second oligonucleotide primer, wherein the first and second primers, in the presence of mammalian genomic DNA and under polymerase chain reaction conditions, produce a first nucleic acid product corresponding to a region of a SULT1A1 gene and a second nucleic acid product corresponding to a non-polymorphic region of a mammalian genome, and wherein the first and second nucleic acid products are different lengths. The non-polymorphic region of a mammalian genome can be the SULT1A2 gene or the SULT1A3/SULT1A4 gene. The article of manufacture further can include a third oligonucleotide primer and a fourth oligonucleotide primer, wherein the third and fourth primers, in the presence of mammalian genomic DNA and under polymerase chain reaction conditions, produce a third nucleic acid product corresponding to a region of a control gene (e.g., the coagulation factor five gene or GAPDH gene). The first or second primer can be labeled (e.g., with a fluorescent dye or a radioisotope).

In yet another aspect, the invention features a method of determining copy number of a gene. The method includes providing a biological sample containing mammalian genomic DNA; producing first and second nucleic acid products from the biological sample using a first oligonucleotide primer and a second oligonucleotide primer under polymerase chain conditions, the first nucleic acid product corresponding to a region of a target gene and the second nucleic acid product corresponding to a non-polymorphic region of a mammalian genome, and wherein the first and second nucleic acid products are different lengths, and determining copy number based on the relative proportion of the first and second nucleic acid products. The target gene can be the human SULT1A gene. The non-polymorphic region of the mammalian gene can be the human SULT1A2 or SULT1A3/SULT1A4 gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 5A shows enzymatic activity derived from 267 liver samples, while FIG. 5B shows activity derived from 33 selected platelet samples. The number above each column represents the number of samples tested in each group.

DETAILED DESCRIPTION

Figure 1:
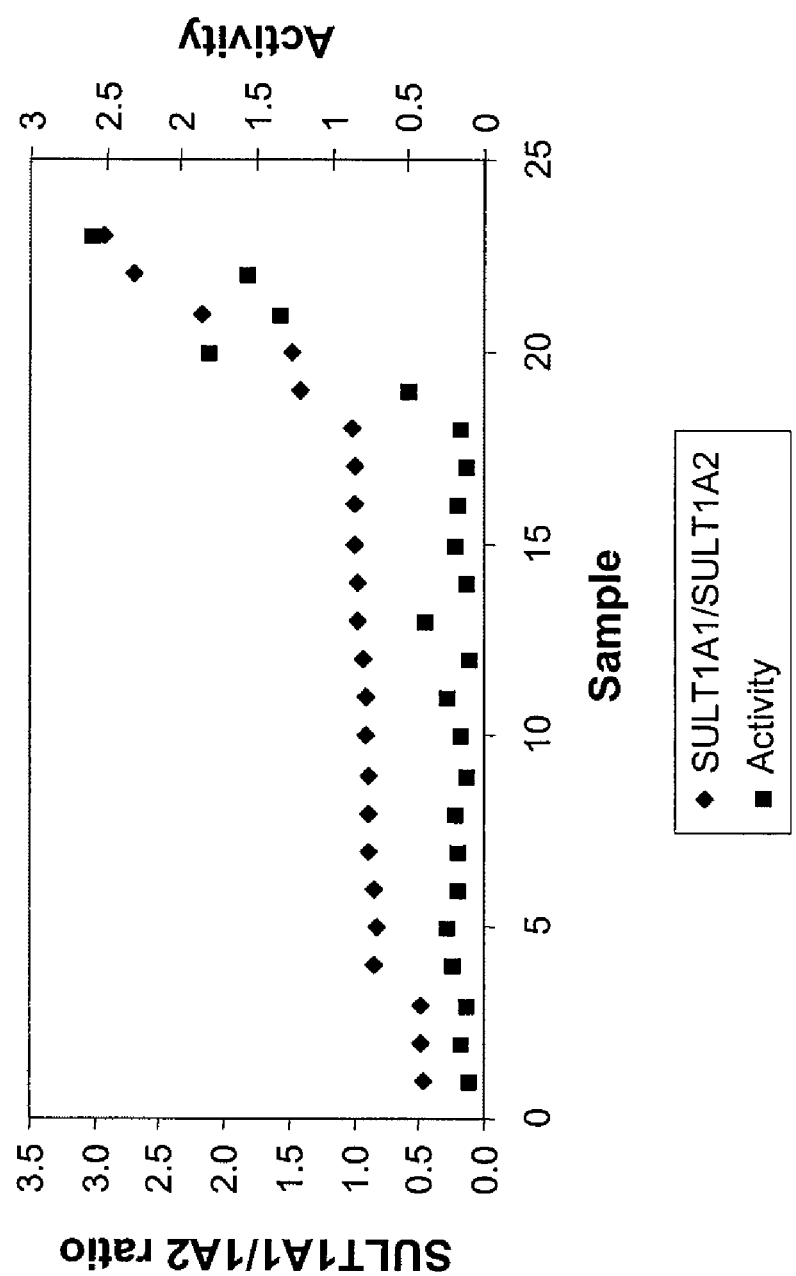
FIG. 1 is a graph of the ratio of SULT1A1/SULT1A2 copy number (diamonds) and corresponding SULT1A1 activity (squares).

In general, the invention provides methods and materials for determining sulfonator status of a mammal (e.g., a human) based on the copy number of the SULT1A1 gene. "Sulfonator status" refers to the ability to transfer a sulfate group to a substrate. In particular, SULT1A1 catalyzes the transfer of inorganic sulfate to molecules such as dopamine, epinephrine, acetaminophen, 17β-estradiol (E2), diethylstilbestrol, 1-napthol, 4-hydroxytamoxifen, minoxidil, estrone (E1), genistein, catechin hydrate, epicatechin, epigallocatechin gallate, quercetin, myricetin, kaempferol, caffeic acid chlorgenic acid, n-propyl gallate, resveratrol, nitrophenol, and other monocyclic phenols, and uses 3'-phosphoadenosine-5'-phosphosulfate (PAPS) as the sulfate donor. Sulfonation typically detoxifies compounds, as the resulting ionized, organic sulfates are more readily excreted than the unsulfated compounds. Furthermore, functional groups that may interact with biological macromolecules such as nucleic acids or proteins can be masked by the sulfate moiety. Certain substrates, however, become more reactive upon sulfonation. For example, the N-hydroxy metabolite of 2-acetylaminoflourene is converted to a N—O-sulfate ester, which is reactive with biological macromolecules. Thus, determining copy number of the SULT1A1 gene can facilitate the prediction of therapeutic efficacy and toxicity of drugs on an individual basis since individuals carrying 3 or more copies of the SULT1A1 gene can be greater metabolizers of numerous drugs, and as such, have inadequate therapeutic responses due to a higher metabolism rate. Conversely, individuals with <2 copies of the SULT1A1 gene can be at risk for toxicity due to decreased metabolism of drugs. In addition, alterations in SULT1A1 copy number may play a role in cancers, including, for example, breast cancer (and increased breast density after oral estrogen, a risk factor for breast cancer), colon cancer, esophageal, and lung cancer.

Determining Copy Number of a Gene

SULT1A1 chromosomal copy number can be detected by any DNA, RNA (e.g., Northern blotting), or protein (e.g., Western blotting or protein activity) based method. Non-limiting examples of DNA based methods include quantitative PCR; fluorescence in situ hybridization (FISH); Southern blotting; multiple amplifiable probe hybridization (MAPF, see Hollox et al., 2002, *Expert Rev. Mol. Diagn.*, 2(4):370-8.); multiplex ligation-dependent probe amplification (MLPA, see Schouten et al., 2002, *Nucleic Acids Res.*, 30(12):e57, kits available from MRC-Holland, Amsterdam, The Netherlands); QMPSF (Quantitative Multiplex PCR of Short Fluorescent Fragments, see Casilli et al., 2002, *Hum. Mutat.* 20(3):218-26), and combinations of such methods.

Typically, genomic DNA is used in the analysis of copy number. Genomic DNA can be extracted from any biological sample containing nucleated cells, such as a peripheral blood sample or a tissue sample (e.g., mucosal scrapings of the lining of the mouth or from renal or hepatic tissue). Standard methods can be used to extract genomic DNA from a blood or tissue sample, including, for example, phenol extraction. Alternatively, genomic DNA can be extracted with kits such as the QIAamp® Tissue Kit (Qiagen, Valencia, Calif.), Wizard® Genomic DNA purification kit (Promega, Madison, Wis.) and the A.S.A.P.™ Genomic DNA isolation kit (Boehringer Mannheim, Indianapolis, Ind.).

Quantitative PCR assays can include quantitative-fluorescent PCR (QF-PCR) assays and real-time quantitative PCR assays such as the TaqMan® assay (Applied Biosystems, Foster City, Calif.) or the LightCycler® assay (Roche Diagnostics Corporation, Indianapolis, Ind.). QF-PCR generally involves the amplification of genomic DNA using a pair of primers. Typically, one of the primers (e.g., the forward primer) is labeled with a fluorescent molecule to allow the size and amount of the amplified PCR product to be assessed.

As described herein, quantitative PCR also can be performed using a pair of oligonucleotide primers that co-amplify two fragments, a fragment from the gene of interest and a copy number control fragment from a non-polymorphic region of DNA. The amplified fragments differ in length from each other by at least 1 nucleotide (e.g., 2, 3, 4, 5, 6, 7, 8, 9, 10, 15, or more nucleotides), and can be 30, 40, 50, 60, 70, 80 90, 100, 125, 150, 175, 200, 225, 250, 300, 350, 400, or more nucleotides in length. Oligonucleotide primer pairs can amplify, for example, one or more exons, portions of exons, or introns or other non-coding sequences in the target sequences. For example, a pair of primers can amplify a region from the human SULT1A1 gene and a region from a different human SULT1A gene such as the SULT1A2 or SULT1A3/SULT1A4 gene. SULT1A3 is duplicated on human chromosome 16 and is referred to as SULT1A3/SULT1A4 herein. See, Hildebrandt et al. (2004) *Biochem. Biophys. Res. Commun.* 321(4):870-8. The genomic and coding sequences of the human SULT1A1 gene are set forth in GenBank Accession Nos. U52852 and AB062428, respectfully. The genomic and coding sequences of the human SULT1A2 gene are set forth in GenBank Accession Nos. U28170 and NM_177528, respectfully; and genomic and coding sequences of the human SULT1A3 gene are set forth in GenBank Accession Nos. U20499 and NM_003166, respectfully. The oligonucleotide primers having the nucleotide sequences set forth in SEQ ID NO:4 and SEQ ID NO:5 are examples of primers that co-amplify fragments from the SULT1A1 (a 212 nucleotide fragment) and SULT1A2 (a 208 nucleotide fragment) genes.

In some embodiments, a quantitative PCR reaction can include one or more additional oligonucleotide primer pairs. For example, an oligonucleotide primer pair can be included such that an extra copy number control fragment is amplified. Suitable control fragments are from a non-polymorphic region of a mammalian genome (e.g., human genome) and include, for example, a region from the coagulation factor five or the glyceraldehyde-3-phosphate dehydrogenase (GAPDH) gene.

Typically, oligonucleotide primers are 10 to 50 nucleotides in length and can be combined with genomic DNA from a mammal and subjected to PCR conditions as set out below, to co-amplify a product that corresponds to a region of a gene of interest (e.g., the SULT1A1 gene) and a non-polymorphic region of a mammalian genome (e.g., a SULT1A2, or SULT1A3/SULT1A4 gene). Specific PCR conditions typically are defined by the concentration of salts (e.g., $MgCl_2$) in the reaction buffer, and by the temperatures utilized for melting, annealing, and extension. Specific concentrations or amounts of primers, templates, deoxynucleotides (dNTPs), and DNA polymerase also may be set out. For example, PCR conditions with a buffer containing 2.0 mM $MgCl_2$, and melting, annealing, and extension temperatures of 94° C., 55° C.-64° C. (e.g., 58° C.), and 72° C., respectively, are particularly useful. Under such conditions, a PCR sample can include, for example, 15 ng genomic DNA, 6 µM of each primer, 200 µM dNTPs, 1 U DNA polymerase (e.g., AmpliTaq Gold from Applied Biosystems), and the appropriate amount of buffer as specified by the manufacturer of the polymerase (e.g., 1× AmpliTaq Gold buffer). Denaturation, annealing, and extension each may be carried out for 30 seconds per cycle, with a total of 20 to 40 cycles (e.g., 23 cycles). An initial denaturation step (e.g., 94° C. for 2-10 minutes) and a final elongation step (e.g., 72° C. for 10 minutes) also may be useful.

Typically, one primer of each primer pair is labeled such that the amplified product can be detected. In embodiments in which multiple pairs of primers are used, each primer pair can be labeled with a different moiety such that multiple amplifications can be carried out in the same reaction. Suitable labels, include, for example, radioisotopes (e.g., $^{125}$I, $^{131}$I, $^{35}$S, $^{3}$H, $^{32}$P, $^{33}$P, or $^{14}$C), fluorescent moieties (e.g., fluorescein, carboxyfluorescein, fluorescein-5-isothiocyanate (FITC), PerCP, rhodamine, or phycoerythrin (PE)), luminescent moieties (e.g., Qdot™ nanoparticles supplied by the Quantum Dot Corporation, Palo Alto, Calif.), or compounds that absorb light of a defined wavelength. Methods of detecting or quantifying a label depend on the nature of the label and are known in the art. Examples of detectors include, without limitation, x-ray film, radioactivity counters, scintillation counters, spectrophotometers, calorimeters, fluorometers, luminometers, and densitometers.

Amplified products can be separated based on size (e.g., in a slab-gel system or by capillary electrophoresis) and the appropriate detection system used to determine the relative proportion of the amount of amplified product from the gene of interest to the amount of amplified product from the copy number control(s). In particular, an automated system for separating and detecting the amplified products, such as the ABI PRISMS® 3100 capillary electrophoresis system from Applied Biosystems, can be used to separate the PCR products and determine the height ratio of the different amplified products to discriminate the copy number of the gene of interest. An approximate 1:1 ratio of the amount of product from the gene of interest to the amount of product from the copy number control indicates that copy number is normal (i.e., copy number is 2). An increase in the ratio of the amount of product from the gene of interest to the amount of product from the copy number control indicates that the copy number is increased (i.e., 3 or more copies), whereas a decrease in the ratio indicates that the copy number is decreased (i.e., 1 copy).

If the copy number control is a duplicated gene (i.e., 4 copies), the amount of product from the gene of interest to the amount of product from the copy number control can be performed as described above and the copy number adjusted accordingly. For example, a 1:1 ratio of the amount of product from the gene of interest to the amount of product from the copy number control of a duplicated gene indicates that the copy number of the gene of interest also is 4. An increase in the ratio of the amount of product from the gene of interest to the amount of product from the copy number control indicates that the copy number is increased (i.e., 5 or more copies). A decrease in the ratio can indicate that the copy number is normal or decreased, depending on the amount of product from the gene of interest. For example, a 1:2 ratio of the amount of product from the gene of interest to the amount of product from the copy number control indicates that copy number is normal and a 1:4 ratio indicates that copy number is decreased.

Assessing Sulfonator Status and Determining Dosages of Drugs

SULT1A1 copy number can be used to determine sulfonator status of a mammal or to determine the dosage of a drug to be administered to a patient. In general, methods of the invention include determining the copy number of the SULT1A1 gene in a biological sample from a patient (e.g., a human patient) relative to one or more regions of a control gene (e.g., the SULT1A2 gene and/or coagulation factor five gene). Methods for detecting copy number are described above.

In some embodiments, copy number can be correlated with sulfonator status. An increase in the copy number (e.g., 3, 4, 5, or 6 copies) of the SULT1A1 gene can result in an enhanced sulfonator status and an increased capacity for sulfonating substrates. A decrease in the copy number of the SULT1A1 gene can result in a decreased sulfonator status and a reduced capacity for sulfonating substrates.

Copy number of the SULT1A1 gene also can be used to determine the dosage of a drug that is a substrate for SULT1A1, including, for example, estrogens such as estrone (E1), 17β-estradiol (E2), 2-hydroxyestrone, 2-hydroxyestradiol, 4-hydroxyestrone, and 4-hydroxyestradiol; synthetic estrogens such as diethylstilbestrol, 4-hydroxytamoxifen, and 2-methoxy estradiol; catecholamines and derivatives such as dopamine and tyramine; serotonin derivates such as 5-hydroxyindole and 6-hydroxymelatonin; drugs such as paracetamol, minoxidil, acetaminophen, and troglitazone; genistein, or other monocyclic phenols. An increase in copy number is indicative of an increased capacity for sulfonating substrates and as such, dosage of the drug may need to be increased to achieve an adequate therapeutic response. A decrease in copy number is indicative of a reduced capacity to sulfonate substrates and as such, dosage of the drug may need to be reduced to prevent toxicity. Additional factors to consider when determining the appropriate dosage of a drug can include the route of administration, the size, weight, surface area, age, and/or sex of the subject, or other drugs being administered. Dosages can be adjusted using standard empirical routines for optimization, as is well understood in the art.

Articles of Manufacture

Oligonucleotide primer pairs described herein can be combined with packaging materials and sold as articles of manufacture or kits for detecting copy number of a gene. Components and methods for producing articles of manufactures are well known. The articles of manufacture may combine one pair of oligonucleotide primers or a plurality of oligonucleotide primer pairs (e.g., 2, 3, 4, or more than 4 primer pairs). For example, an article of manufacture can include first and second oligonucleotide primers, which, in the presence of mammalian genomic DNA and under polymerase chain reaction conditions, produce a first nucleic acid product corresponding to a region of a SULT1A1 gene and a second nucleic acid product corresponding to a non-polymorphic region of a mammalian genome (e.g., a SULT1A2, or SULT1A3/SULT1A4 gene). In some embodiments, third and fourth oligonucleotide primers can be included in the article of manufacture that, in the presence of mammalian genomic DNA and under polymerase chain reaction conditions, produce a third nucleic acid product corresponding to a region of a control gene. Oligonucleotide primers can be labeled with a detectable moiety, for example, a fluorescent dye or radioisotope.

In addition, an article of manufacture further can include sterile water, pharmaceutical carriers, buffers, antibodies, indicator molecules, DNA polymerase, nucleotides, and/or other useful reagents for detecting copy number of a gene.

Instructions describing how oligonucleotide primers can be used in an assay to detect copy number of a gene (e.g., SULT1A1) can be included in such kits.

The invention will be further described in the following examples, which do not limit the scope of the invention described in the claims.

EXAMPLES

Example 1

Materials And Methods

DNA: DNA was obtained from the Coriell Cell Repository (Camden, N.J., U.S.A.). Specifically, 100 samples each from the two 100-item sample sets, HD100CAU and HD100AA, were used. All of the DNA samples had been anonymized by the National Institutes of Health prior to their deposit in the Coriell Cell Repository, and all subjects had provided written consent for the use of their DNA for experimental purposes.

Total genomic DNA samples, which were previously isolated from 23 of 33 blood samples by Raftogianis et al. ((1997) *Biochem. Biophys. Res. Commun.* 239(1):298-304), also were used. Platelet homogenates for these same samples had previously been prepared and phenotyped for SULT1A1 activity. See Van Loon and Weinshilboum (1984) *Biochem. Genet.* 22(11-12):997-1014; and Price et al. (1989) Genetics 122(4): 905-14.

DNA also was obtained from human hepatic surgical biopsy samples obtained from 268 Caucasian women having clinically-indicated surgery, predominantly for the diagnosis and/or treatment of metastatic carcinoma. Normal hepatic tissue from the site of tumor was used to perform the studies described herein.

Genotyping: Arg213His SNP genotyping was conducted using a PSQ 96 (Biotage, Uppsala, Sweden). PCR primers 5'/5BioTEG/GTTGGCTCTGCAGGGTCTC TAGGA-3' (SEQ ID NO:1) and 5'-CCCAAACCCCCGTACTGGC-CAGCACCC-3' (SEQ ID NO:2) amplified a 333 bp fragment. Each 15 µL PCR reaction contained 15 ng lymphocyte DNA template, 0.6 µM of each primer, 200 µM dNTPs, 2.0 mM $MgCl_2$, and 1.0 U AmpliTaq Gold (Applied Biosystems). The PCR reaction consisted of a 10 minute incubation at 95° C., then 40 cycles of denaturation at 94° C. for 30 seconds, annealing at 63.5° C. for 30 seconds, and extension at 72° C. for 30 seconds, with a final extension at 72° C. for 10 minutes on a PTC-225 (MJ Research). The separation of double strand to single strand was conducted according to the Vacuum Prep Tool manual (Biotage). The sequencing reaction was conducted according to PSQ 96 protocol with sequencing primer

5'-CGGTCTCCTCTGGCA-3'. (SEQ ID NO:3)

Genotypes for -396 (rs750155) and -624 (rs3760091) were acquired using fluorescent-based allele specific PCR with the analysis performed on an ABI3100 DNA analyzer (Applied Biosystems). Each 15 µL PCR reaction contained 15 ng lymphocyte DNA template, 0.6 µM of forward and total reverse primer, 200 µM dNTPs, 2.0 mM $MgCl_2$, and 1.0 U AmpliTaq Gold (Applied Biosystems). The PCR reaction consisted of a 10 minute incubation at 95° C., followed by 26 cycles of denaturation at 94° C. for 30 seconds, annealing at 67° C. for 30 seconds, and extension at 72° C. for 30 seconds, with a final extension at 72° C. for 10 minutes on a PTC-225 (MJ Research). Primers for rs750155 included a forward primer (5'-6FAM/TCATCATCCTGCCTGGTTAATG-3', SEQ ID NO:4) and two reverse primers differentially tailed representing the two possible nucleotides at this position (5'-GTTTAGCGCCCTTTGTCTCACCAC-3', SEQ ID NO:5, and 5'-GTTTATAGCGCCC TTTGTCTCACCAT-3', SEQ ID NO:6). Primers for rs3760091 included a forward primer (5'6FAM/T CATCATCCTGCCTGGTTAATG-3', SEQ ID NO:4) and three reverse primers differentially tailed to represent the three possible nucleotides at this position (5'-GTTTCTGATGACTCAGCA AAAGCAA-3', SEQ ID NO:7; 5'-GTTTACCTGATGACTCAGCAAAAGCAC-3', SEQ ID NO:8; and 5'-GTTTACGT CTGATGACTCAG-CAAAAGCAG-3', SEQ ID NO:9).

Gene Duplication Assay—fluorescent-based quantitative PCR: The set of PCR primers designed for this assay (5'6FAM/TCACCGAGCTCCCATCTT-3' (SEQ ID NO:10), located in exon 3, and 5'-GGGGCAGGTGTGTCTTCAG-3' (SEQ ID NO:11), located in exon 4 of the SULT1A1 gene) co-amplify a 212 bp fragment within SULT1A1 and a 208 bp fragment within SULT1A2, which is used as a control copy number reference. In addition, a pair of primers (5'6FAM/ATGGACTTCCACATTAGGGAC-3' (SEQ ID NO:12) and 5'-GAAGGTAGTGGATTCTCCATCA-3' (SEQ ID NO:13)) that amplify a 202 bp region from the coagulation factor five gene was included as an additional copy number control. Each PCR reaction contained 15 ng template lymphocyte DNA, 0.6 µM of each primer, 200 µM dNTPs, 2.0 mM $MgCl_2$, and 1.0 U AmpliTaq Gold (Applied Biosystems) in a 15 µL reaction. The PCR reaction consisted of a 10 minute incubation at 95° C., then 23 cycles of denaturation at 94° C. for 30 seconds, annealing at 58° C. for 30 seconds, and extension at 72° C. for 30 seconds, with a final extension at 72° C. for 10 minutes on a PTC-225 (MJ Research).

Fragments were run on an ABI3100 (Applied Biosystems). By measuring the height ratio of the 212 bp amplicon of SULT1A1 to the reference 208 bp amplicon of SULT1A2, individuals were differentiated with one through >4 copies of SULT1A1.

Haploid Analysis: EBV transformed lymphocytes of three samples known to carry a deletion of SULT1A1 were subjected to haploid conversion. Hybrid cell lines were generated by fusing lymphoblastoid cells from subjects with E2 mouse cells essentially as described by Yan et al. ((2000) *Nature* 403:723-724). Using a number of microsatellite markers, mouse/human hybrid cell lines were screened to isolate clones containing individual chromosome 16 alleles: one clone containing the intact SULT1A1 gene and another clone with the deleted allele. The extent of the deletion in each case was then examined directly by testing DNA for the presence or absence of PCR amplification using six primer pairs spaced along the 5' and 3' region of SULT1A1 (FIG. 2): R1 5'-TCAGCAACCTTCAGGAGGC-3' (SEQ ID NO:14) and 5'-TGCCT GGGATTTTCTGTTGT-3' (SEQ ID NO:15); R2 5'-TGCAGGAAATCTGCCTACG-3' (SEQ ID NO:16) and 5'-GTGCCACCAGGCTTGACTA-3' (SEQ ID NO:17; R3 5'-CTC AGGATGCTGTGACCTT-3' (SEQ ID NO:18) and 5'-TGTCAGTTTGCTGACCCTT-3' (SEQ ID NO:19); R4 5'-TCTTGACCCCAGAGTGAACA-3' (SEQ ID NO:20) and 5'-GAGTGTCTTCAAACAGGACCA-3' (SEQ ID NO:21); R5 5'-TCAGCAACCCTC AGGAGGT-3' (SEQ ID NO:22) and 5'-TGCCTGGGATTTTGTATTCA-3' (SEQ ID NO:23); and R6 (5'-ATGTCACAGGCATGCCCT-3' (SEQ ID NO:24) and 5'-CGGG AGAATTGCTTGAAAGA-3' (SEQ ID NO:25). As a PCR control, a mouse STS marker (MEG1) (5'-AAATGACGACTCCGTGTAACC-3' (SEQ ID NO:26) and 5'-TTAACA CCCTCTGCATTCCC-3' (SEQ ID NO:27)) was co-amplified in a multiplex with the six primer pairs. Each PCR reaction contained 15 ng template lymphocyte DNA, 0.6 µM of each primer, 200 µM dNTPs, 2.0 mM $MgCl_2$, and 1.0 U AmpliTaq Gold (Applied Biosystems) in a 15 µL reaction. The PCR reaction consisted of a 10 minute incubation at 95° C., followed by 23 cycles of denaturation at 94° C. for 30 seconds, annealing at 55° C. (R1, R2, R4, and R6) or 58° C. (R3 and R5) for 30 seconds, and extension at 72° C. for 30 seconds, with a final extension at 72° C. for 10 minutes on a PTC-225 (MJ Research). As a PCR control, a mouse STS marker (MEG1) was co-amplified in a multiplex with the six primer pairs. The PCR products were then run on a 2% agarose gel and visualized directly after staining with ethidium bromide.

Reporter Gene Constructs and Promoter Activity: SULT1A1 5'-FR sequences that contain the common SNPs located at positions (−624) and (−396) were used to create firefly luciferase reporter gene constructs in pGL3-Basic vector (Prondzinski et al. (2003) *Clin. Pharmacol. Ther.* 73:77). Nucleotide locations were numbered relative to the "A" in the SULT1A1 translation initiation codon. These constructs were 700 bp in length, and contained all possible haplotypes for the two SNPs (−624 C/G, −396 G/A). These constructs were sequenced in both directions to ensure that the correct sequences were present and were then used to transfect HepG2 and HEK293 cells. Specifically, 2 µg purified plasmid DNA were transfected into the cells together with 20 ng pRL-TK (Promega) DNA. The *Renilla* luciferase activity expressed by pRL-TK was used as a control for transfection efficiency. Cells were also transfected with pGL3-Basic that lacked an insert as a control. Results of these reporter gene studies were reported as the ratio of firefly luciferase to *Renilla* luciferase light units, and values were expressed relative to the activity of the pGL3-Basic vector construct. All assays were performed in triplicate in both cell lines and were repeated three times, for a total of nine independent data points.

Statistical Analysis: To test the effect of genotype versus the effect of copy number on level of activity, linear regression models were used. The first model was for the effect of copy number, regardless of allele type, and used the total number of allele copes as the independent predictor of activity level. The second model considered the role of particular allele types, and used the counts of each particular allele type as the predictors of activity level (i.e., requiring two independent predictors). Comparing the second model versus the first, by a likelihood ratio test, provided an evaluation of the role of particular alleles, over the effect of copy number, on level of activity. A small p-value would suggest that specific alleles influence activity level over the effect of total copy number, whereas a large p-value would suggest specific alleles do not contribute to activity level, once the total copy number is accounted for. Comparing the first model versus a model without any predictors provided a test of the total copy number.

Enzyme Activity: Platelet homogenates from 23 blood samples were previously phenotyped for SULT1A1 activity as described elsewhere (Raftogianis et al. (1997) *Biochem. Biophys. Res. Commun.* 239:298-304). SULT1A1 enzyme activity in the liver samples were measured by modifications of the method of Foldes and Meek ((1973) *Biochim. Biophys. Acta* 327:365-374) as described by Campbell et al. ((1987) *Biochem. Pharmacol.* 36:1435-1446).

Example 2

Duplication of SULT1A1 and Functional Implications of Copy Number Differences

In genotyping the SULT1A1 polymorphism Arg213His using a semi-quantitative sequencing assay (PSQ 96), it was observed that some of the Arg213His heterozygotes showed unusual peak distribution, suggesting that one allele was preferentially being amplified over the other. After confirming that there were no polymorphisms under the primer sequences and that SULT1A2, SULT1A3, or SULT1A4 were not being coamplified, it was hypothesized that these differences were caused by a polymorphic duplication of the gene.

A set of primers was designed that would co-amplify SULT1A1 and SULT1A2 equally but produce amplicons of different sizes. To confirm SULT1A2 also was not being duplicated or deleted, a secondary control amplicon (Factor five) that was multiplexed with SULT1A1 and SULT1A2 was included in the assay. The same 100 Caucasian and 100 African-American samples that had been genotyped were tested using the fluorescent-based quantitative PCR assay described in Example 1. It was found that with the heterozygotes with unusual peak patterns, extra copies of the SULT1A1 gene were present. Not only were individuals identified with multiple copies of SULT1A1, two individuals were identified that were carriers of only one copy of SULT1A1. In the Caucasian population, 2.1% were carriers of one SULT1A1 copy and 22.1% had greater than two copies. In comparison, the African American population had no carriers of the gene deletion, while 62.6% had greater than two copies (Table 1). By looking at Arg213His in relation to copy number, it appears that SULT1A1*1 is the allele that is predominately, although not exclusively, duplicated. At least four of the samples carry duplicated SULT1A1*2 alleles. When comparing the pyrosequencing results to the fluorescent-based quantitative PCR assay results, virtually every sample that had uneven quantities of the SULT1A1*1 and 1A1*2 alleles had more than two alleles of SULT1A1.

The frequency of SULT1A1 copy number also was determined as described above for 267 liver samples from Caucasian subjects (Table 1). Among all of the Caucasian subjects, 17 of 362 samples (4.7%) demonstrated a deletion within the SULT1A1 gene, i.e., one copy, while 93 subjects (26%) had three or more copies.

Within the 23 platelet samples with known SULT1A1 activity, three samples were identified carrying the deleted genotype while five samples had greater then two copies of the gene. These five samples showed an increase in SULT1A1 activity (FIG. 1) and the greater the number of alleles, the higher the activity (rho 0.8406, p<0.0001). This trend was not observed within the samples with only one allele. Because two allele activities are already low, the assay may not be sensitive enough to be able to pick up a further drop in activity caused by samples carrying only one allele.

Figure 2:
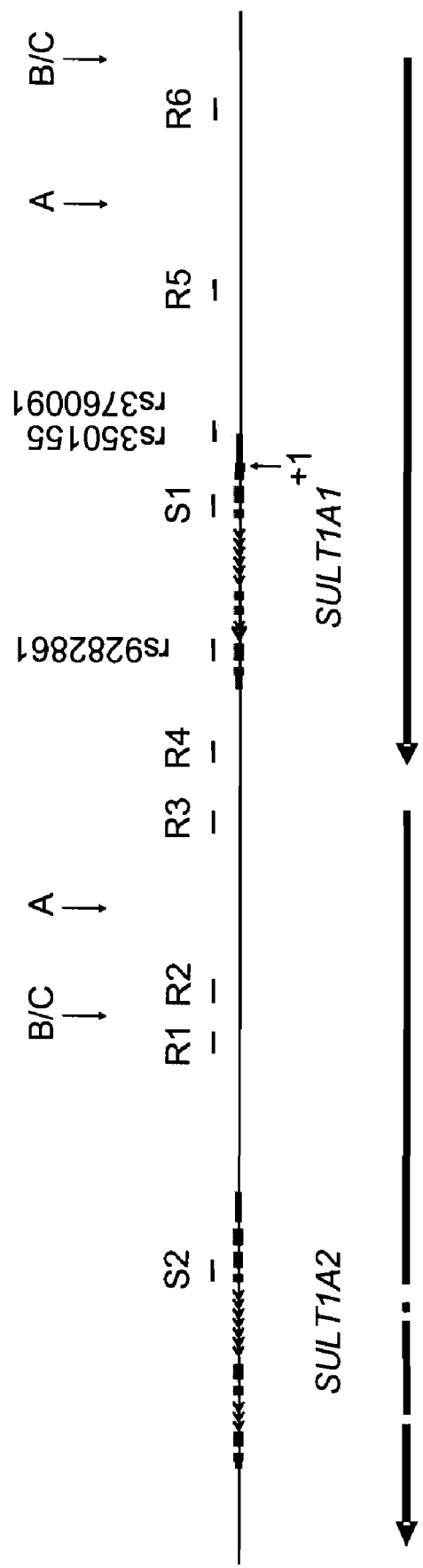
FIG. 2 is a diagram of the gene structure of SULT1A1 (NM$_{13}$ 177534) and SULT1A2 (NM__177528). Numbering the A in the ATG start site as +1, primer positions for the various assays are as follows: copy number control (S1, +13448 to +13242), map set 1 (R1, +10739 to +10595), map set 2 (R2, +10196 to +9965), map set 3 (R3, +6125), map set 4 (R4, +4682 to +4506), Arg213His rs9282861 (+2829 to +2497), copy number (S2, +524 to +314), rs350155 and rs376001 (−379 to −772), map set 5 (R5, −2255 to −2399), and map set 6 (R6, −5499 to −5677). Arrows below represent regions of high homology between SULT1A1 and SULT1A2, while arrows above represent breakpoints for subjects A, B, C.
Figure 3:
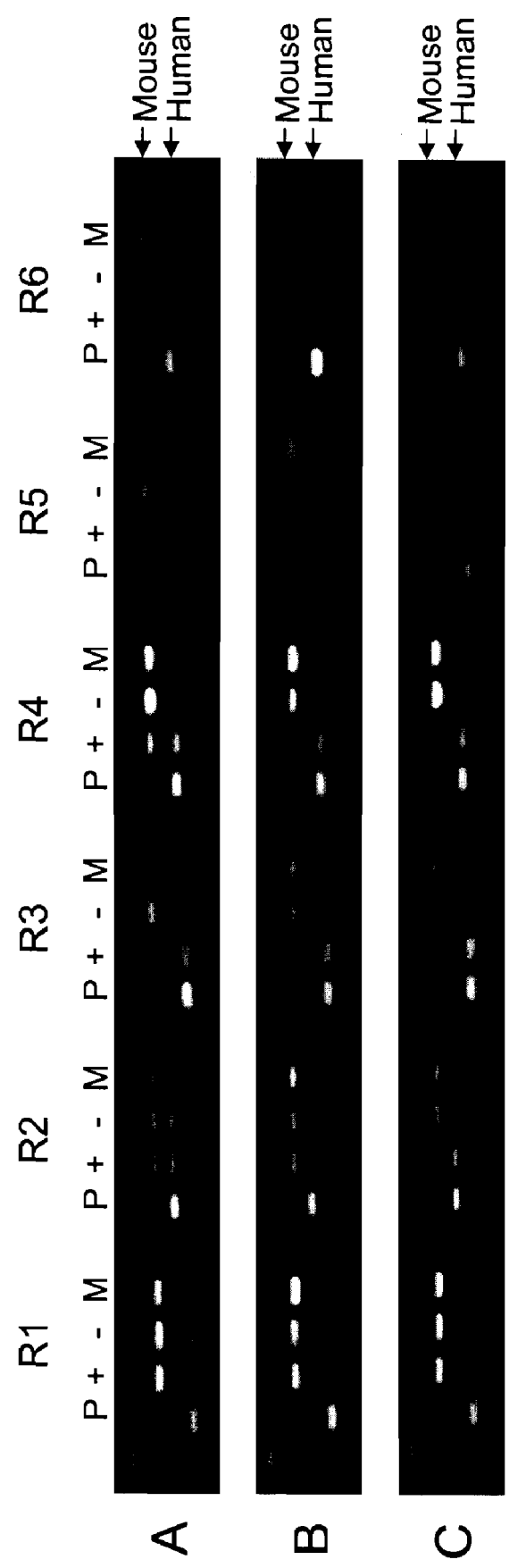
FIG. 3 shows the results of PCR analysis of three samples (A, B, and C) subjected to haploid mapping. For each parental sample (P), two haplotype cell lines were identified: chromosome 16 with intact SULT1A1 (+), and chromosome 16 with a deleted allele (−). In addition, mouse only DNA (M) was used as a control. Six PCR primer sets for regions R1 through R6 were utilized in a multiplex with mouse STS marker MEG1.

In order to define the extent of the genomic alterations, the region surrounding the SULT1A1 gene was further analyzed in three cases found to have a deletion. Haploid cell lines were created by fusing E2 mouse cells with lymphoblastoid cells obtained from these 3 subjects, and the lines were screened for clones containing only a single human chromosome 16. PCR analysis was then performed utilizing primers for 6 genomic regions (FIG. 2, labeled R1-R6). Results of the PCR deletion mapping for all three of these cases (DNA from the original lymphocytes, the cell lines with intact SULT1A1, and the cell lines with deleted SULT1A1, along with mouse only DNA) are shown in FIG. 3. Based on this analysis, at least two different deletions were identified. For sample A, the 3' breakpoint of SULT1A1 occurs in a 3.6 kb region between primers R2 and R3, while the 5' breakpoint lies within a 3.1 kb region between R5 and R6. For both samples B and C, the 3' deletion breakpoint occurs between R1 and R2 while the 5' breakpoint extends beyond R6 (FIGS. 2 and 3). Overall, these data demonstrate that the breakpoints flank the coding region and that the entire SULT1A1 gene is deleted. It is presumed that gene duplications have similar breakpoints. Because the 5' and 3' ends of SULT1A1 share such high homology, it is likely that homologous recombination is the mechanism for these deletion and duplication events.

Figure 4A:
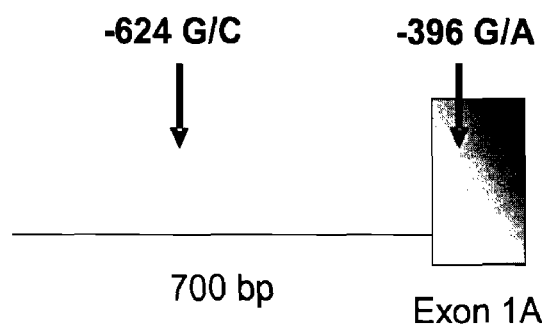
FIG. 4A is a diagram indicating the positions of the SNPs (−624 and −396) in the SULT1A1 reporter constructs used in transfection assays.
Figure 4B:
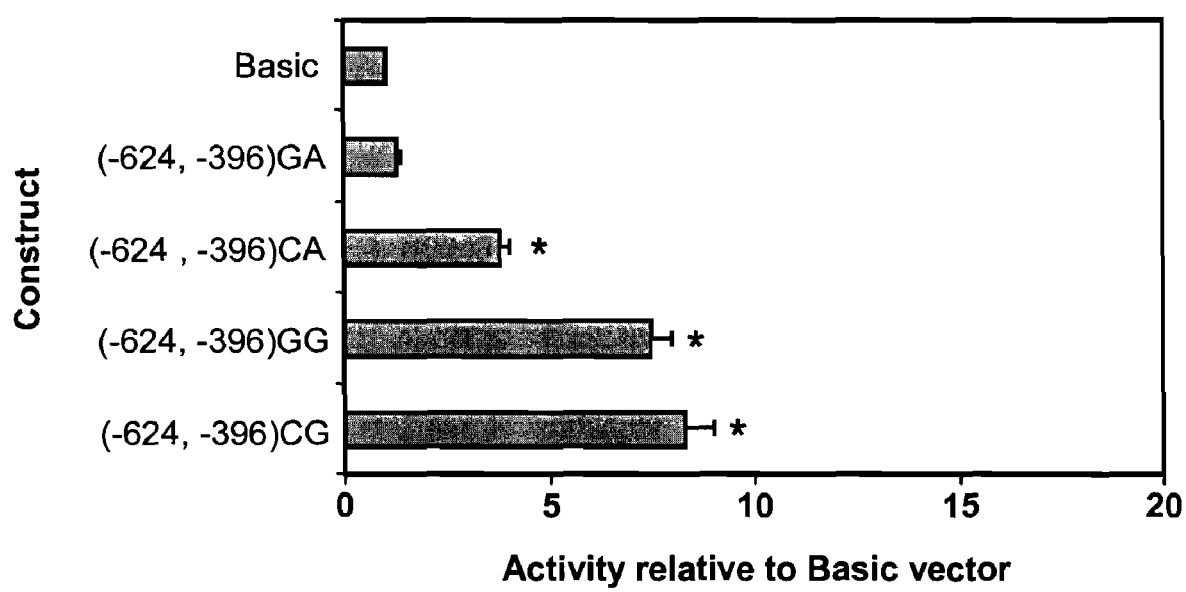
FIG. 4B is a graph plotting results from reporter gene studies. Luciferase activity was measured in extracts from HepG2 cells transfected with SULT1A1 reporter constructs containing each of the four combinations of bases (wild type and variant) at positions −624 and −396. Values represent mean±SEM (N=6–9), and * represents P<0.0001 for activity when compared to the basic vector.

In addition to the G638A SNP, two 5'-FR polymorphisms also have been reported to play a role in the variability observed in SULT1A1 enzymatic activity. In an effort to explore the functional significance of these two 5'-FR SNPs (−624 and −396; FIG. 4A), luciferase reporter gene assays were performed with constructs containing the four possible haplotypes of the SULT1A1 5'-FR SNPs. After transfection into HepG2 and HEK293 cells, the CG, GG, CA and GA haplotypes showed 8.3-fold, 7.5-fold, 3.8-fold and 0-fold increases (N=6-9) in luciferase activity, respectively, when compared to pGL-3 Basic (FIG. 4B). These results further support the idea that these polymorphic variants may contribute to differences in SULT1A1 enzymatic activity.

Previous studies of SULT1A1 genotype-phenotype correlation, which have focused primarily on the G638A SNP and the two 5'-FR polymorphisms, have been performed in the absence of knowledge of the SULT1A1 gene duplication. Thus, to further determine whether variations in the SULT1A1 copy number and the three SNPs are associated with alteration in function, both the copy number genotype and phenotype for SULT1A1 were derived for 23 platelet samples and 267 liver samples; 18 (6%) of the 267 samples carried the deleted allele while 78 (27%) had more then two copies of the gene. Using the gene copy data in conjunction with a quantitative SNP assay, the number of alleles for the G638A SNP and the two promoter SNPs were defined in the liver samples. The effect of genotype versus the effect of copy number on level of activity was then determined. Overall, there did not appear to be a significant effect of a particular allele above the effect of the total copy number on the level of

TABLE 1

Figure 5A:
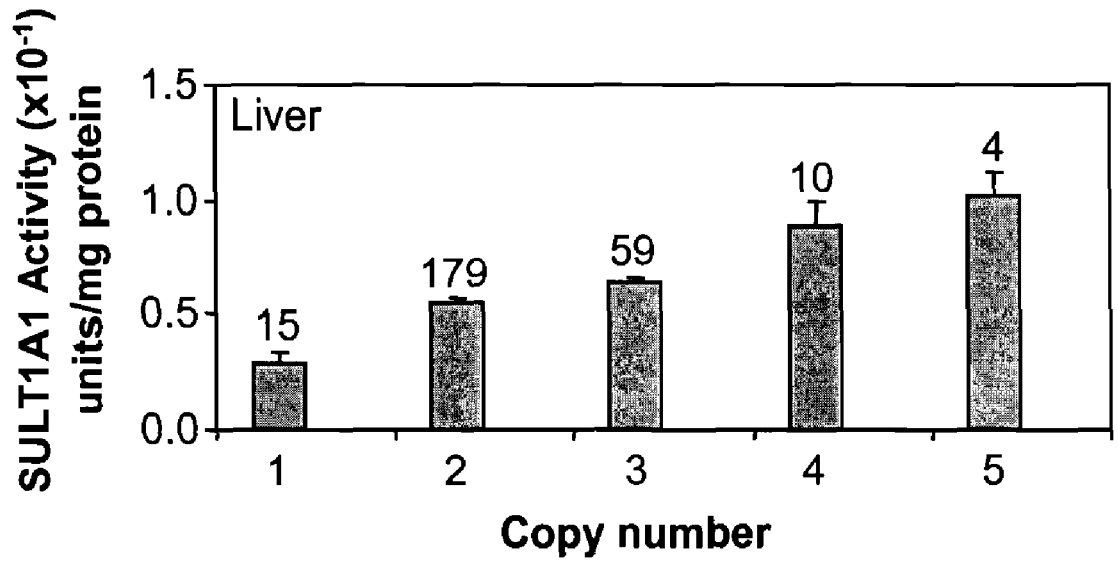
FIGS. 5A and 5B are graphs plotting the enzymatic level of SULT1A1 derived from different tissues as a function of copy number.
Figure 5B:
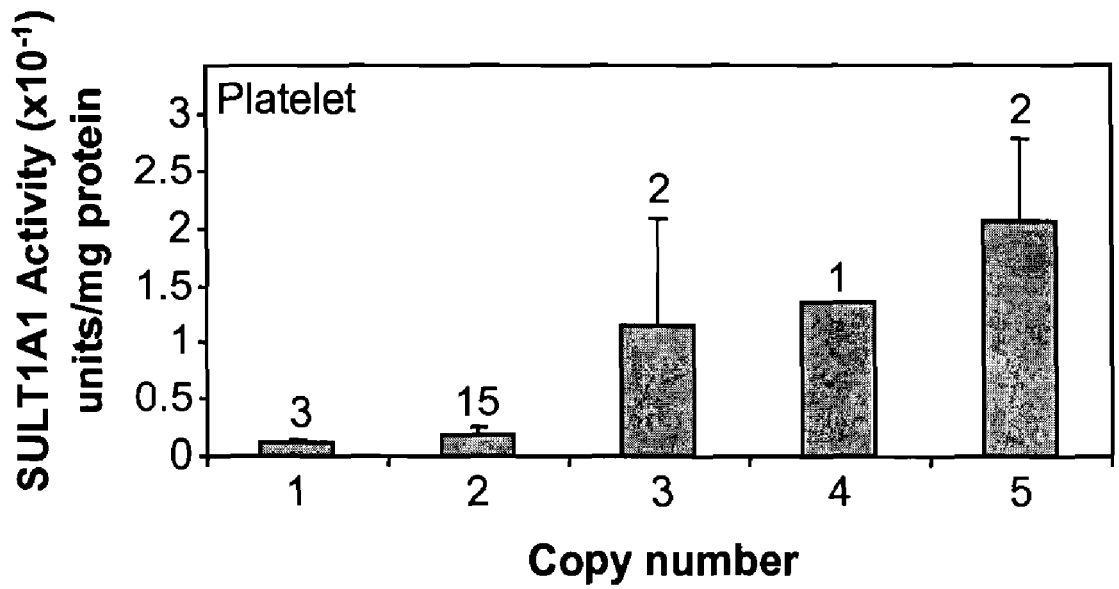

| samples | 1 allele | 2 alleles | 3 alleles | 4 alleles | >4 alleles | >2 alleles |
|---|---|---|---|---|---|---|
| CA Coriell (n = 95) | 2 (2.1%) | 73 (76.8%) | 17 (17.9%) | 3 (3.2%) | 0 | 20 (21.1%) |
| CA Liver (n = 267) | 15 (5.6%) | 179 (67.0%) | 59 (22.1%) | 10 (3.7%) | 4 (1.5%) | 73 (27.3%) |
| TOTAL (n = 362) | 17 (4.7%) | 252 69.6%) | 76 (21.0%) | 13 (3.6%) | 4 (1.1%) | 93 (25.7%) |
| AA Coriell (n = 99) | 0 | 37 (37.4%) | 37 (37.4%) | 21 (21.2%) | 4 (4.0%) | 62 (62.6%) | activity for each of the three SNPs tested: 5'-FR (−624), rs3760091; 5'-FR (−396), rs750155; and G638A, rs9282861 (p=0.61, 0.77, and 0.67, respectively) with respect to SULT1A1 activity. The total copy number, however, did have a very strong effect (p<0.0001) with respect to enzyme activity. For each increase in copy number, there was an estimated 0.15 (95% CI: 0.11-0.19) associated increase in enzymatic activity ($\times 10^{-1}$ unit/mg) (FIG. 5A). A more pronounced effect was seen when enzyme activity in platelets was compared to SULT1A1 copy number (FIG. 5B).

Taken together, these data indicate that SULT1A1 gene copy number differences explain the majority of the variation in SULT1A1 activity in liver and platelets when all of the known sources of genetic variability are taken into account. The presence of multiple copies of SULT1A1 appears to be common, with frequencies that vary with ethnicity. Twenty-six percent of Caucasians and 63% of the African American subjects studied had more than two alleles. In addition, 5% of the Caucasian subjects had a single copy of the SULT1A1 gene, while none of the African American subjects tested had this genotype (Table 2). Individuals carrying additional copies of SULT1A1 represent "rapid sulfators," while those with fewer copies are "slow sulfators." The pharmacogenetic implications of differences in SULT1A1 gene dosage might help explain individual differences in drug toxicity and/or efficacy in the clinical setting. Additionally, it should now be possible to consider SULT1A1 gene dosage as an independent variable when studying the possible association of this gene with complex phenotypes and/or disease susceptibility.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a relative level of SULT 1A1 activity in a human subject, said method comprising:
   a) providing a biological sample comprising genomic DNA from said subject;
   b) analyzing said genomic DNA to determine the copy number of the SULT1A1 gene in said biological sample; and
   c) correlating copy number of the SULT1A1 gene with SULT1A1 activity in said subject, wherein more than two copies of the SULT1A1 gene is indicative of an increased level of SULT1A1 activity, and wherein two or less copies of the SULT1A1 gene is indicative of a decreased level of SULT1A1 activity.

2. The method of claim 1, wherein said biological sample is a blood or tissue sample.

3. The method of claim 1, wherein copy number of the SULT1A1 gene is detected by a quantitative PCR assay.

4. The method of claim 3, wherein said quantitative PCR assay is a fluorescent quantitative PCR assay.

5. The method of claim 1, wherein copy number of the SULT1A1 gene is detected by fluorescence in situ hybridization.

6. The method of claim 1, wherein copy number of the SULT1A1 gene is detected by Southern blotting.

7. The method of claim 1, wherein copy number of the SULT1A1 gene is detected by multiplex ligation-dependent probe amplification (MLPA).

8. The method of claim 1, wherein copy number of the SULT1A1 gene is detected by Quantitative Multiplex PCR of Short Fluorescent Fragments (QMPSF).

* * * * *

SEQUENCE LISTING

```
<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gttggctctg cagggtctct agga                                              24

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
cccaaacccc cgtactggcc agcaccc                                           27

<210> SEQ ID NO 3
<211> LENGTH: 15
<212> TYPE: DNA
<213> ORGANISM: Artificial Sequence
<220> FEATURE:
<223> OTHER INFORMATION: Primer

<400> SEQUENCE: 3
cggtctcctc tggca                                                        15

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tcatcatcct gcctggttaa tg                                                22

<210> SEQ ID NO 5
<211> LENGTH: 24
<212> TYPE: DNA
<213> ORGANISM: Artificial Sequence
<220> FEATURE:
<223> OTHER INFORMATION: Primer
```

```
<400> SEQUENCE: 5
gtttagcgcc ctttgtctca ccac                                          24

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
gtttatagcg ccctttgtct caccat                                        26

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
gtttctgatg actcagcaaa agcaa                                         25

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
gtttacctga tgactcagca aaagcac                                       27

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
gtttacgtct gatgactcag caaaagcag                                     29

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tcaccgagct cccatctt                                                 18

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
ggggcaggtg tgtcttcag                                                19

<210> SEQ ID NO 12
```

```
<211> LENGTH: 21
<212> TYPE: DNA
<213> ORGANISM: Artificial Sequence
<220> FEATURE:
<223> OTHER INFORMATION: Primer

<400> SEQUENCE: 12
atggacttcc acattaggga c                                                 21

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
gaaggtagtg gattctccat ca                                                22

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
tcagcaacct tcaggaggc                                                    19

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tgcctgggat tttctgttgt                                                   20

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
tgcaggaaat ctgcctacg                                                    19

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
gtgccaccag gcttgacta                                                    19

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
```

-continued ctcaggatgc tgtgaccct                                              19

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
tgtcagtttg ctgaccctt                                              19

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tcttgacccc agagtgaaca                                             20

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gagtgtcttc aaacaggacc a                                           21

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
tcagcaaccc tcaggaggt                                              19

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tgcctgggat tttgtattca                                             20

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
atgtcacagg catgccct                                               18

<210> SEQ ID NO 25
<211> LENGTH: 20
<212> TYPE: DNA

-continued

```
<213> ORGANISM: Artificial Sequence
<220> FEATURE:
<223> OTHER INFORMATION: Primer

<400> SEQUENCE: 25
cgggagaatt gcttgaaaga                                              20

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
aaatgacgac tccgtgtaac c                                            21

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ttaacaccct ctgcattccc                                              20
```